(12) United States Patent
Lester (10) Patent No.: US 10,287,078 B2
(45) Date of Patent: May 14, 2019

(54) PRODUCT PACKAGING

(71) Applicant: C.R. Bard, Inc., Murray Hill, NJ (US)

(72) Inventor: Jessica L. Lester, McDonough, GA (US)

(73) Assignee: C.R. Bard, Inc., Murray Hill, NJ (US)

( * ) Notice: Subject to any disclaimer, the term of this patent is extended or adjusted under 35 U.S.C. 154(b) by 84 days.

(21) Appl. No.: 15/475,254

(22) Filed: Mar. 31, 2017

(65) Prior Publication Data

US 2018/0282042 A1   Oct. 4, 2018

(51) Int. Cl.

| | |
|---|---|
| *B05C 19/04* | (2006.01) |
| *B65D 75/58* | (2006.01) |
| *B65D 83/08* | (2006.01) |
| *B65D 81/22* | (2006.01) |
| *B65D 75/30* | (2006.01) |
| *B08B 1/00* | (2006.01) |
| *B65D 8/00* | (2006.01) |

(52) U.S. Cl.
CPC .......... *B65D 75/5855* (2013.01); *B08B 1/006* (2013.01); *B65D 9/02* (2013.01); *B65D 75/30* (2013.01); *B65D 81/22* (2013.01); *B65D 83/0805* (2013.01); *B65D 83/0894* (2013.01); *A45D 2200/1036* (2013.01); *A45D 2200/1045* (2013.01); *B65D 2221/00* (2013.01)

(58) Field of Classification Search
CPC .... A45D 2200/1036; A45D 2200/1045; A45D 2200/1009; A45D 2200/1018; A45D 2200/1027; B65D 75/30; B65D 75/5855; B65D 9/02

See application file for complete search history.

(56) References Cited

U.S. PATENT DOCUMENTS

| | | | |
|---|---|---|---|
| 1,791,351 A * | 2/1931 | Fielding Chase | A45D 33/34 132/320 |
| 5,242,433 A | 9/1993 | Smith et al. | |
| 6,008,429 A | 12/1999 | Ritger | |
| 9,079,208 B2 * | 7/2015 | Gundersen | A45D 37/00 |
| 9,884,717 B2 * | 2/2018 | Tsujimura | A45D 44/002 |

(Continued)

FOREIGN PATENT DOCUMENTS

| | | |
|---|---|---|
| EP | 0360925 | 4/1990 |
| WO | PCT/US18/18640 | 5/2018 |

*Primary Examiner* — Jennifer C Chiang
(74) *Attorney, Agent, or Firm* — Dorton & Willis LLP; Ryan Willis (57) ABSTRACT

A dispensing and applicator system comprising: (a) a first and second moisture impermeable layers removably coupled to one another to delineate a first interior cavity; (b) a first applicator pad operatively coupled to an interior side of the first moisture impermeable layer and located within the first interior cavity; (c) a second applicator pad operatively coupled to an interior side the second moisture impermeable layer and located within the first interior cavity when the first and second moisture impermeable layers are coupled to one another; (d) a first finger flap operatively coupled to an exterior side of the first moisture impermeable layer, where the exterior side of the first moisture impermeable layer is opposite the interior side; and, (e) a second finger flap operatively coupled to an exterior side of the second moisture impermeable layer, where the exterior side of the second moisture impermeable layer is opposite the interior side.

29 Claims, 8 Drawing Sheets

(56) References Cited

U.S. PATENT DOCUMENTS

| | | | |
|---|---|---|---|
| 2008/0025787 A1* | 1/2008 | Shea | A45D 34/04 |
| | | | 401/265 |
| 2011/0094919 A1* | 4/2011 | Roempp | A47K 10/421 |
| | | | 206/524.1 |
| 2011/0174650 A1 | 7/2011 | Kimball | |
| 2018/0199694 A1* | 7/2018 | Mehta | A45D 37/00 |

* cited by examiner

PRODUCT PACKAGING

INTRODUCTION TO THE INVENTION

The present disclosure is directed to product packaging and, more specifically, to product packaging configured to expose sealed contents to a field of use without necessarily exposing the contents to contamination prior to introduction into the field of use.

Disinfecting pads, commonly referred to as "prep pads," are frequently used to guard against infection from germs (including, but not necessarily limited to bacteria, viruses, fungi, and protozoa) by bringing the pads into contact with surfaces needing disinfecting. Exemplary applications include disinfecting needle injection sites or incision sites, killing bacteria on surfaces to prevent contamination, infection or susceptibility to illness, and wiping epidermal areas prior to application of an adhesive as part of ostomy seals. While the prep pads need not entrain sterile fluids, it is within the scope of the disclosure for the prep pads to entrain fluids such as, without limitation, ethanol and iodine.

A frequent problem with existing prep pads is accessing the pads without contamination or tearing the pad. By way of example, current industry packaging for prep pads includes welded seals circumscribing an internal prep pad, thereby requiring a user to tear open the packaging and potentially tearing the prep pad. Even in instances where tearing the packaging does not tear the prep pad, the pad is often caught in the tearing process, not allowing a smooth continuous opening of the package. Furthermore, the tearing of the package may introduce particulate into the site, potentially compromising the safety of the patient when the setting is in a sterile field. The user is then nonetheless required to "fish" out the pad using his/her fingers. But grasping the pad via the user's fingers exposes the prep pads to various forms of contamination, and exposing the user's fingers to the active chemicals of the prep pad. Moreover, current industry packaging requires that a user hold or discard portions of the torn packaging (creating multiple pieces of the packaging in addition to at least one piece of the prep pad) prior to or during use of the prep pad, thereby limiting hand mobility during application. Consequently, there is a need in the art for packaging addressing at least some of the shortcomings of the current packaging.

In addressing the outstanding need in the industry for product packaging, the instant disclosure provides a sealed package that is able to be opened to discontinue the seal and expose the internal contents for use. In exemplary form, the instant disclosure provides packaging having finger gripping tabs on an exterior of the packaging that facilitate discontinuing of the packaging seal, as well as a grasping location allowing a user to access the interior of the packaging and make use of the internal contents without contamination from direct contact with the user's hands. In exemplary form, in the context of a prep pad, the interior product (prep pad) may remain sterile until the product is applied to the desired site/location. Moreover, the exemplary product packaging may be configured to create no separable trash or other waste requiring disposal prior to utilizing the internal product. In addition, the product packaging of the instant disclosure may be resealable and/or may provide for multiple internal products to be deployed at sequential different times.

It is a first aspect of the present invention to provide a dispensing and applicator system for applying a plurality of applicator pads comprising: (a) a first and second moisture impermeable layers removably coupled to one another via a first peelable seal to delineate a first interior cavity; (b) a first applicator pad operatively coupled to an interior side of the first moisture impermeable layer and located within the first interior cavity when the first and second moisture impermeable layers are coupled to one another; (c) a second applicator pad operatively coupled to an interior side the second moisture impermeable layer and located within the first interior cavity when the first and second moisture impermeable layers are coupled to one another; (d) a first finger flap operatively coupled to an exterior side of the first moisture impermeable layer, where the exterior side of the first moisture impermeable layer is opposite the interior side; and, (e) a second finger flap operatively coupled to an exterior side of the second moisture impermeable layer, where the exterior side of the second moisture impermeable layer is opposite the interior side.

In a more detailed embodiment of the first aspect, the system further includes: (f) a third moisture impermeable layer removably coupled to the second moisture impermeable layer via a second peelable seal to delineate a second interior cavity, wherein the second seal is weaker than the first seal; (g) a third applicator pad operatively coupled to an interior side of the third moisture impermeable layer and located within the second interior cavity when the third and second moisture impermeable layers are coupled to one another; and, (h) a third finger flap operatively coupled to an exterior side of the third moisture impermeable layer, where the exterior side of the third moisture impermeable layer is opposite the interior side. In yet another more detailed embodiment, the system further includes: (i) a fourth moisture impermeable layer removably coupled to the third moisture impermeable layer via a third peelable seal to delineate a third interior cavity, wherein the third seal is weaker than the second seal; (j) a fourth applicator pad operatively coupled to an interior side of the fourth moisture impermeable layer and located within the third interior cavity when the third and fourth moisture impermeable layers are coupled to one another; and, (k) a fourth finger flap operatively coupled to an exterior side of the fourth moisture impermeable layer, where the exterior side of the fourth moisture impermeable layer is opposite the interior side. In a further detailed embodiment, the system further includes: (l) a fifth moisture impermeable layer removably coupled to the fourth moisture impermeable layer via a fourth peelable seal to delineate a fourth interior cavity, wherein the fourth seal is weaker than the third seal; (m) a fifth applicator pad operatively coupled to an interior side of the fifth moisture impermeable layer and located within the fourth interior cavity when the fourth and fifth moisture impermeable layers are coupled to one another; and, (n) a fifth finger flap operatively coupled to an exterior side of the fifth moisture impermeable layer, where the exterior side of the fifth moisture impermeable layer is opposite the interior side. In still a further detailed embodiment, the first finger flap is substantially flush with the exterior side of the first moisture impermeable layer, and the second finger flap is substantially flush with the exterior side of the second moisture impermeable layer. In a more detailed embodiment, the first finger flap is flush with the exterior side of the first moisture impermeable layer, and the second finger flap is flush with the exterior side of the second moisture impermeable layer. In a more detailed embodiment, at least one of the first peelable seal and the second peelable seal comprises at least one of a laser seal, a sonic induction seal, and a heat seal. In another more detailed embodiment, at least one of the first finger flap and the second finger flap includes a tacky exterior component. In yet another more detailed embodiment, at least one of the first and second moisture impermeable layers comprise at least one of a polyester, a polyethylene, aluminum, and a nylon. In still another more detailed embodiment, at least one of the first and second moisture impermeable layers is adhered to at least one of the first and second applicator pads. In yet another more detailed embodiment, at least one of the first and second applicator pads entrains at least one of ethanol and iodine.

In yet another more detailed embodiment of the first aspect, the system further includes: a third and fourth moisture impermeable layers removably coupled to one another via a second peelable seal to delineate a second interior cavity; a third applicator pad operatively coupled to an interior side of the third moisture impermeable layer and located within the second interior cavity when the third and fourth moisture impermeable layers are coupled to one another; a fourth applicator pad operatively coupled to an interior side the fourth moisture impermeable layer and located within the second interior cavity when the third and fourth moisture impermeable layers are coupled to one another; a third finger flap operatively coupled to an exterior side of the third moisture impermeable layer, where the exterior side of the third moisture impermeable layer is opposite the interior side; and, a fourth finger flap operatively coupled to an exterior side of the fourth moisture impermeable layer, where the exterior side of the fourth moisture impermeable layer is opposite the interior side, wherein at least one of (i) the second third finger flaps are operatively coupled to one another, and, (ii) the second and third moisture impermeable layers are operatively coupled to one another. In yet another more detailed embodiment, the third finger flap is nested and interposes the second finger flap and the second moisture impermeable layer. In a further detailed embodiment, the second finger flap is nested and interposes the third finger flap and the third moisture impermeable layer. In still a further detailed embodiment, a fifth and sixth moisture impermeable layers removably coupled to one another via a third peelable seal to delineate a third interior cavity; a fifth applicator pad operatively coupled to an interior side of the fifth moisture impermeable layer and located within the third interior cavity when the fifth and sixth moisture impermeable layers are coupled to one another; a sixth applicator pad operatively coupled to an interior side the sixth moisture impermeable layer and located within the third interior cavity when the fifth and sixth moisture impermeable layers are coupled to one another; a fifth finger flap operatively coupled to an exterior side of the fifth moisture impermeable layer, where the exterior side of the fifth moisture impermeable layer is opposite the interior side; and, a sixth finger flap operatively coupled to an exterior side of the sixth moisture impermeable layer, where the exterior side of the sixth moisture impermeable layer is opposite the interior side, where at least one of (i) the fourth and fifth finger flaps are operatively coupled to one another, and, (ii) the fourth and fifth moisture impermeable layers are operatively coupled to one another. In a more detailed embodiment, the fifth finger flap is nested and interposes the fourth finger flap and the fourth moisture impermeable layer. In a more detailed embodiment. In another more detailed embodiment, the fourth finger flap is nested and interposes the fifth finger flap and the fifth moisture impermeable layer.

It is a second aspect of the present invention to provide a method of dispensing and using one or more applicator pads comprising: (a) grasping a first finger flap operatively coupled to an exterior side of a first moisture impermeable layer, where the exterior side of the first moisture impermeable layer is opposite an interior side; (b) grasping a second finger flap operatively coupled to an exterior side of a second moisture impermeable layer, where the exterior side of the second moisture impermeable layer is opposite an interior side; (c) pulling the first and second finger flaps away from one another to break a first peelable seal between the first moisture impermeable layer and the second moisture impermeable layer to expose a first applicator pad previously sealed between the layers; and, (d) contacting a first desired surface with the first applicator pad by using at least one of the first and second finger flaps, where the finger flaps are fluidically separated from the first applicator pad.

In a more detailed embodiment of the second aspect, pulling the first and second finger flaps away from one another to break the first peelable seal between the first moisture impermeable layer and the second moisture impermeable layer exposes a second applicator pad previously sealed between the layers. In yet another more detailed embodiment, pulling the first and second finger flaps away from one another to break the first peelable seal completely separates the first moisture impermeable layer from the second moisture impermeable layer; the first applicator pad is operatively coupled to the first moisture impermeable layer post separation of the first and second moisture impermeable layers; and, the second applicator pad is operatively coupled to the second moisture impermeable layer post separation of the first and second moisture impermeable layers. In a further detailed embodiment, the method further includes: (e) grasping a third finger flap operatively coupled to an exterior side of a third moisture impermeable layer, where the exterior side of the third moisture impermeable layer is opposite an interior side, while grasping the first finger flap; (f) pulling the first and third finger flaps away from one another to break a second seal between the third moisture impermeable layer and the second moisture impermeable layer to expose a second applicator pad previously sealed between the layers; and, (g) contacting a second desired surface with the second applicator pad by using the third finger flap, where the third finger flap is fluidically separated from the second applicator pad. In still a further detailed embodiment, the method further includes: (h) grasping a fourth finger flap operatively coupled to an exterior side of a fourth moisture impermeable layer, where the exterior side of the fourth moisture impermeable layer is opposite an interior side, while grasping the first finger flap; (i) pulling the first and fourth finger flaps away from one another to break a third seal between the third moisture impermeable layer and the fourth moisture impermeable layer to expose a third applicator pad previously sealed between the layers; and, (j) contacting a third desired surface with the third applicator pad by using the fourth finger flap, where the fourth finger flap is fluidically separated from the third applicator pad.

It is a third aspect of the present invention to provide a method of dispensing and using one or more applicator pads comprising: (a) grasping a first finger flap operatively coupled to an exterior side of a first moisture impermeable layer, where the exterior side of the first moisture impermeable layer is opposite an interior side; (b) grasping a second finger flap operatively coupled to an exterior side of a second moisture impermeable layer, where the exterior side of the second moisture impermeable layer is opposite an interior side; (c) pulling the first and second finger flaps away from one another to disengage the first moisture impermeable layer and the second moisture impermeable layer; (d) grasping the first finger flap operatively coupled to the exterior side of the first moisture impermeable layer post disengagement from the second moisture impermeable layer; (e) grasping a third finger flap operatively coupled to an exterior side of a third moisture impermeable layer, where the exterior side of the second moisture impermeable layer is opposite an interior side, where the first and third moisture impermeable layers define a sealed cavity; (f) pulling the first and third finger flaps away from one another to break a peelable seal between the first and third moisture impermeable layers and exposing a first applicator pad previously sealed between the first and third moisture impermeable layers; and, (g) contacting a first desired surface with the first applicator pad by using at least one of the first and third finger flaps, where the finger flaps are fluidically separated from the first applicator pad.

It is a fourth aspect of the present invention to provide a method of fabricating a dispensing system for one or more applicator pads, the method comprising: (a) providing a first moisture impermeable layer that includes an interior face and an opposite exterior face, wherein the exterior face is operatively coupled to a first finger flap; (b) providing a second moisture impermeable layer that includes an interior face and an opposite exterior face, wherein the exterior face is operatively coupled to a second finger flap; and, (c) sealing a first applicator pad between interior faces of the first and second moisture impermeable layers using a first peelable seal.

In yet another more detailed embodiment of the fourth aspect, the method further includes: (d) providing a third moisture impermeable layer that include an interior face and an opposite exterior face, wherein the exterior face is operatively coupled to a third finger flap; and, (e) sealing a second applicator pad between the interior face of the third moisture impermeable layer and the exterior face of the second moisture impermeable layer using a second peelable seal, where a seal between the second and third moisture impermeable layers is weaker than a seal between the first and second moisture impermeable layers. In yet another more detailed embodiment, the method further includes: (f) providing a fourth moisture impermeable layer that include an interior face and an opposite exterior face, wherein the exterior face is operatively coupled to a fourth finger flap; and, (g) sealing a third applicator pad between the interior face of the fourth moisture impermeable layer and the exterior face of the third moisture impermeable layer using a third peelable seal, where a seal between the fourth and third moisture impermeable layers is weaker than a seal between the third and second moisture impermeable layers. In a further detailed embodiment, the first applicator pad includes a pair of applicator pads, one of the pair of applicator pads is mounted to the interior face of the first moisture impermeable layer, and another of the pair of applicator pads is mounted to the interior face of the second moisture impermeable layer. In still a further detailed embodiment, at least one of the first finger flap and the second finger flap includes a living hinge. In a more detailed embodiment, consecutively repeating steps (a) through (c) to generate a plurality of prep pad packages, where each set of steps (a) through (c) generates one of the plurality of prep pad packages, and orienting the plurality of prep pad packages so that every other one is inverted and the first finger flap of one of the plurality of prep pad packages interposes the second finger flap and the second moisture impermeable layer of another of the plurality of prep pad packages.

DETAILED DESCRIPTION

The exemplary embodiments of the present disclosure are described and illustrated below to encompass exemplary product packaging and, more specifically, to product packaging configured to expose sealed contents to a field of use without necessarily exposing the contents to contamination prior to introduction into the field of use. Of course, it will be apparent to those of ordinary skill in the art that the embodiments discussed below are exemplary in nature and may be reconfigured without departing from the scope and spirit of the present invention. However, for clarity and precision, the exemplary embodiments as discussed below may include optional steps, methods, and features that one of ordinary skill should recognize as not being a requisite to fall within the scope of the present invention.

Referencing FIGS. 1-5, a first exemplary product package 100 includes complementary outer walls 102, 104 that are sealed together via a circumferential seal 106 to define an interior cavity. In this exemplary embodiment, the outer walls 102, 104 may be fabricated from one or more polyesters, a polyethylene (including high, moderate, and low density varieties), aluminum, and a nylon. Moreover, the outer walls 102, 104 may be fabricated from a single layer of material, multiple layers of same material, or multiple layers of differing materials such as, without limitation, polyethylene layers sandwiching an aluminum layer therebetween. And the circumferential seal 106 may preferably be configured to comprise a peelable seal.

Within the interior cavity may be housed one or more internal contents that include, without limitation, a prep pad 108 fabricated from an absorbent or sponge material. By way of example, the prep pads 108 may entrain any number of fluids or combinations of fluids such as, without limitation, ethanol and/or iodine. Each outer wall 102, 104 includes a finger flap 110 that is repositionable with respect to the remainder of the respective outer wall and is configured to allow finger gripping between a thumb and complementary finger, for example. In exemplary form, the finger flap 110 may be delineated using a cut or slit 112 formed into a respective outer wall 102, 104 that allows the finger flap to the integral with the outer wall and connected thereto via a living hinge. Alternatively, the finger flap 110 may be a separable component that is mounted to the respective exterior wall 102, 104 using any form of attachment such as, without limitation, heat sealing, laser sealing, adhesive bonding, and vibration sealing. In either instance, it is envisioned that the finger flaps 110 are substantially flat or flush with the topography of the outer walls 102, 104.

Figure 1:
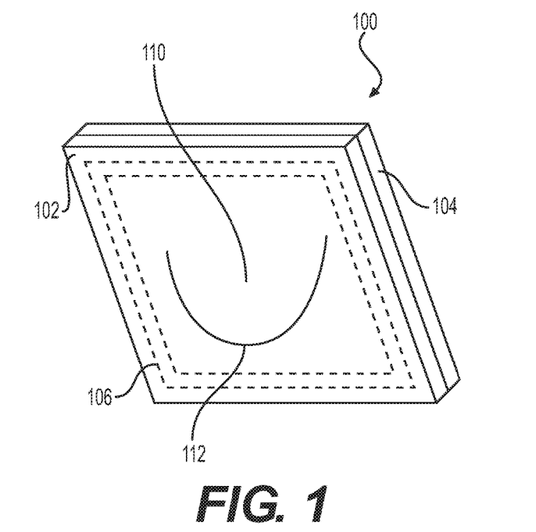
FIG. 1 is an elevated perspective view of a first exemplary product package in accordance with the instant disclosure.
Figure 2:
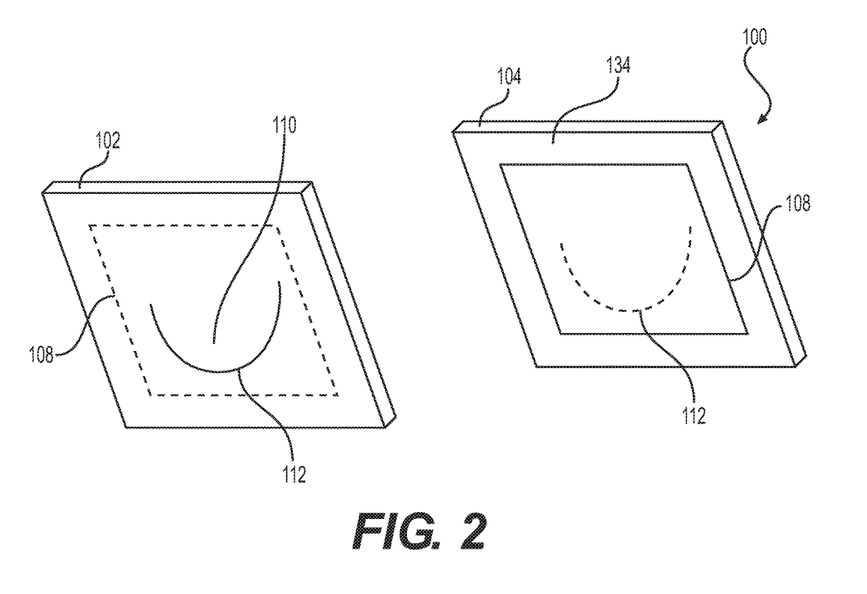
FIG. 2 is an exploded view of the first exemplary product package of FIG. 1.
Figure 3:
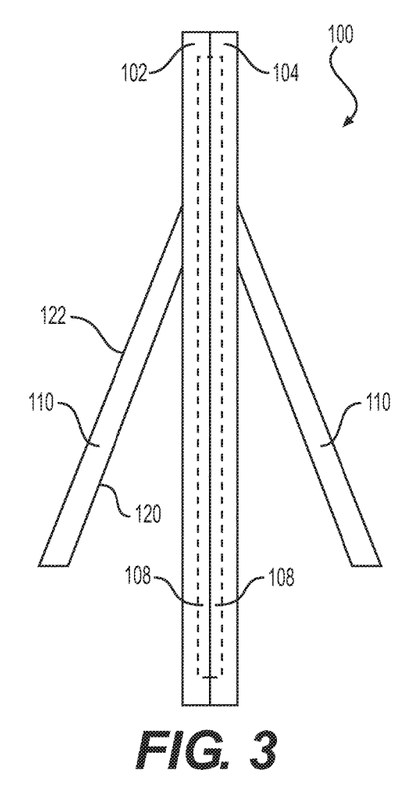
FIG. 3 is a profile view of the first exemplary product package of FIG. 1.
Figure 4:
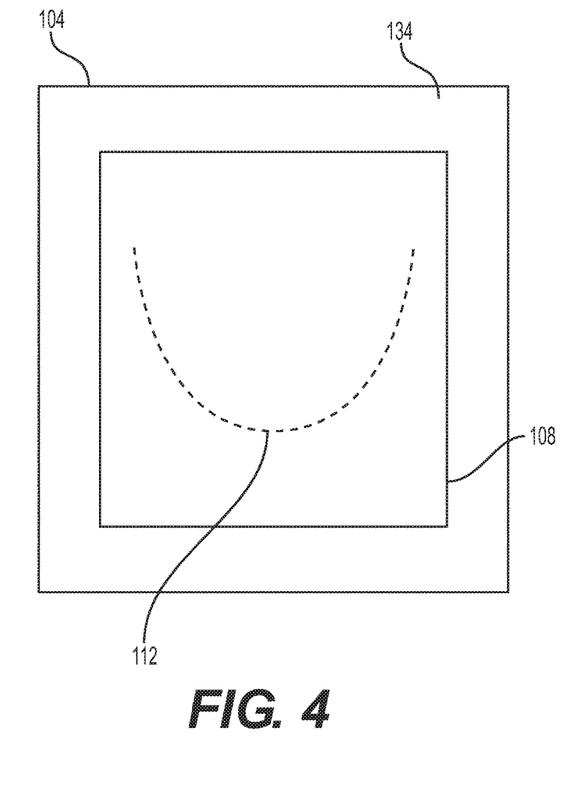
FIG. 4 is an inside surface view of a portion of the first exemplary product package of FIG. 1.

In exemplary form, the product packaging 100 may take on a three-dimensional rectangular shape, with each of the exterior walls 102, 104 having a similar shape. In this fashion, the perimeter of the exterior walls 102, 104 are mounted to one another using the circumferential seal 106 to delineate a generally rectangular internal cavity. It should be noted, however, that shapes other than rectangular are within the scope of the disclosure and include, without limitation, circular, triangular, and shapes with more than four perimeter sides. In this fashion, the circumferential seal 106 may be rectangular, triangular, circular, or take on any shape desired as long as the shape forms a continuous seal around a perimeter of the interior cavity.

The exemplary finger flaps 110 may be grasped and pulled apart as a means to break the circumferential seal 106 of the product packaging 100 and expose the internal contents. In exemplary form, a user of the product packaging 100 may reposition a finger underneath an exposed perimeter 112 of each finger flap 110 to reposition the finger flap away from the generally planar outer wall 102, 104. In so doing, the finger flap 110 protrudes from the outer wall 102, 104 to expose an underneath surface 120 of the finger flap that is generally opposite a top surface 122, which top surface may have been previously lying on top of or coterminous with the outer wall. Upon the exposed perimeter 112 achieving a predetermined separation from a respective outer wall 102, 104, the user may sandwich the surfaces 120, 122 between opposing digits to grasp the finger flap 110 as a means to reposition one outer wall 102 with respect to the other outer wall 104, thereby breaking the circumferential seal 106. In exemplary form, the user grasps the finger flaps 110 and pulls the flaps away from one another (as denoted by the arrows in FIG. 5) to break the seal 106. After the seal 106 is broken, the user may continue to pull the finger flaps 110 to completely separate the outer walls 102, 104 from one another.

Figure 5:
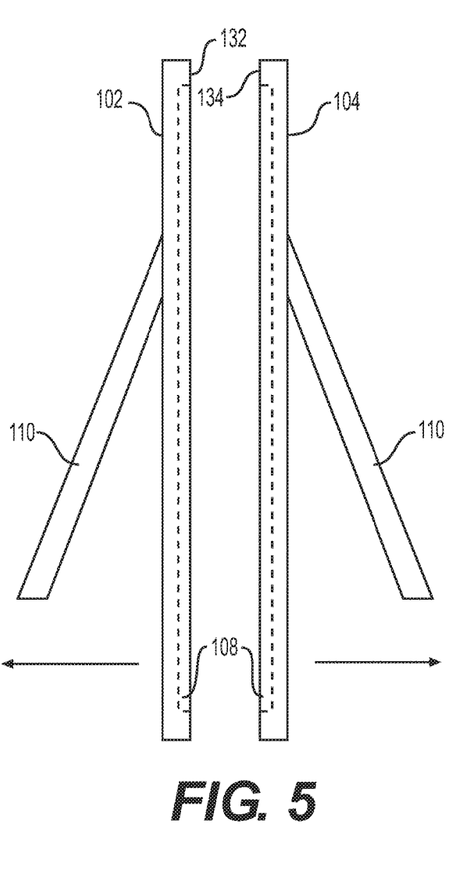
FIG. 5 is a profile view showing intended separation between components of the first exemplary product package of FIG. 1.

In this exemplary embodiment, after the outer walls 102, 104 are completely separated from one another, a pair of prep pads 108 is exposed. By way of example, each of the prep pads 108 is mounted to a corresponding inner face 132, 134 of each wall 102, 104. In this fashion, a face 132, 134 of each wall 102, 104 and the circumferential seal 106 delineate the interior cavity, partially occupied by the prep pads 108. But when the seal 106 is completely broken, an exposed surface of each prep pad 108 becomes available for use. As a result, the user can maintain grasping of one or both of the finger flaps 110 as a means to reposition the exposed prep pads 108 in contact with the desired tissue or surface without requiring the user's fingers or other body part to contact the prep pad and potentially contaminate the prep pad prior to its intended use. Post repositioning of one or both prep pads 108, the user may discard each prep pad 108 and corresponding wall 102, 104 in a trash can or other disposal repository without requiring grasping of the prep pad or regrasping of the finger flap post usage. In other words, the same grasp used to break the circumferential seal 106 may be maintained throughout usage of one or both prep pads 108 and throughout discarding the used prep pad(s). This advantageously avoids the user's hands or other unintended body parts from coming into contact with the prep pad 108 prior to, during, and post usage.

Figure 11:
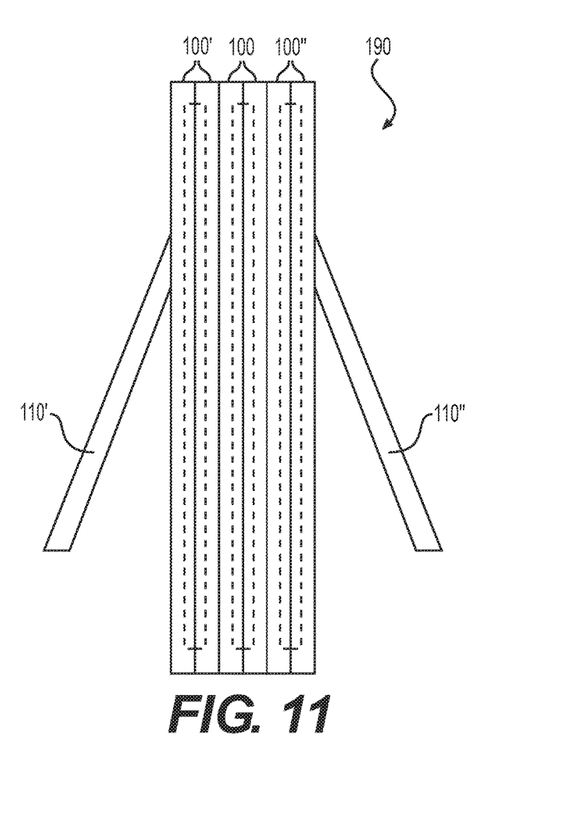
FIG. 11 is a profile view of a compact nesting sleeve comprising a plurality of first exemplary product package of FIG. 1.

Referring to FIGS. 11-15, multiple product packages 100 may be nested with respect to one another as part of bulk packaging or dispenser packaging, thereby comprising a sleeve of product packages in a compact arrangement (see specifically FIG. 11). In exemplary form, the product packages comprising the sleeve 190 may be temporarily interlocked with a preceding product package 100' and subsequent product package 100" without necessitating the aid of adhesives or mechanical break-way fasteners. It should be noted, however, that adhesives and/or break-way fasteners may also be utilized as part of securing adjacent product packages to one another.

Figure 13:
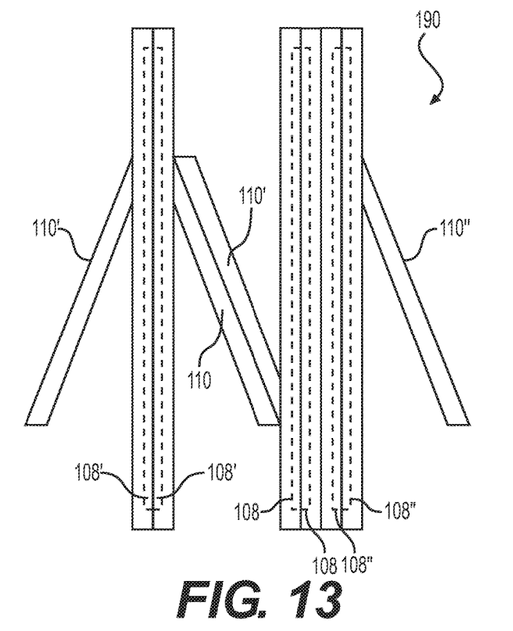
FIG. 13 is a profile view of the compact nesting sleeve of FIG. 11 depicting initial separation of a product package from the remainder of the sleeve.
Figure 15:
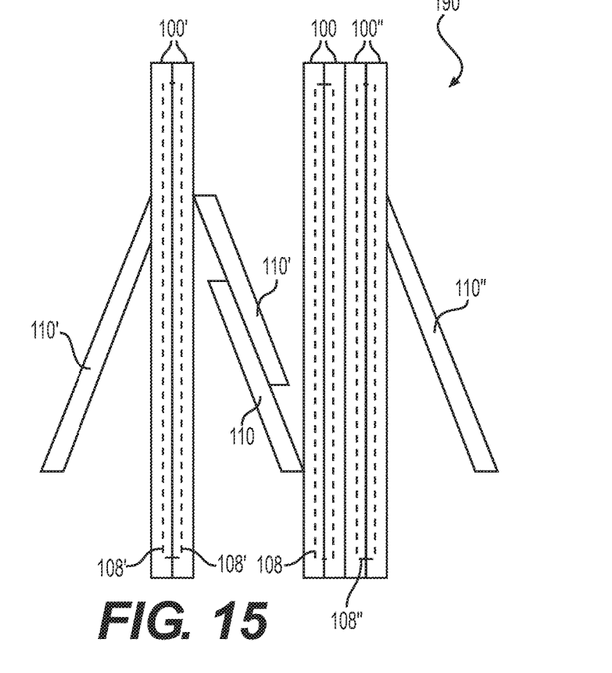
FIG. 15 is a profile view of the nesting sleeve of FIG. 13 depicting further separation of a product package from the remainder of the sleeve.

Referring specifically to FIGS. 13 and 15, a user desiring to use a product package 100' from the sleeve 190 may grasp the outermost finger flap 110' exposed on either end of the sleeve and pull the product package 100' (in exemplary form, the left side outermost product package 100') away from the remainder of the product packages 100, 100" comprising the sleeve. Pulling on the outermost finger flap 110' away from the remaining product packages of the sleeve 190 is operative to create spacing between the adjacent product packages 100', 100 (see FIG. 13) and ready the next product packaging 100 for finger gripping.

Figure 12:
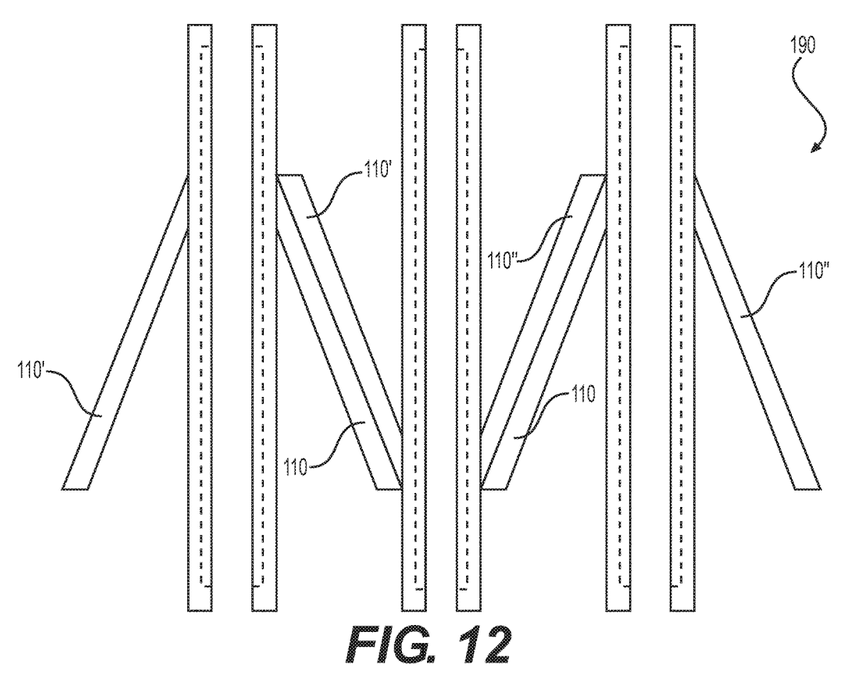
FIG. 12 is a profile view of the nesting sleeve of FIG. 11 depicted in a longitudinal exploded view showing orientation of adjacent finger flaps and separation to expose the previously sealed prep pads.
Figure 14:
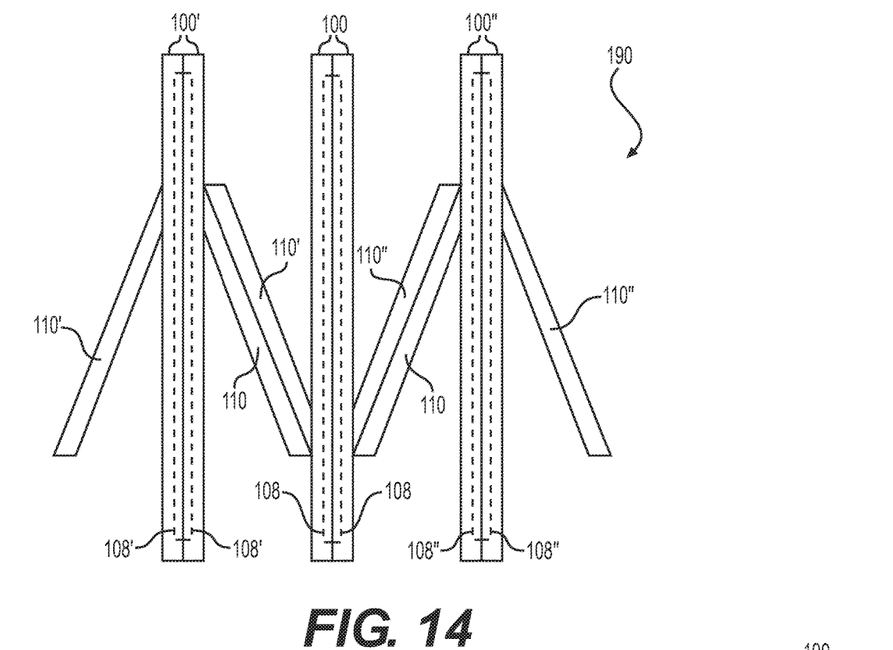
FIG. 14 is a profile view of the nesting sleeve of FIG. 11 depicting separation between adjacent product packages while retaining the prep pads in a sealed configuration.

In exemplary form, the sleeve 190 may comprise three or more product packages 100 loosely attached to one another via overlapping finger flaps 110. More specifically, as depicted in FIGS. 12 and 14, every other product package 100 (in this case, the second product package 100) is inverted with respect to the other two adjacent product packages 100', 100" so that the finger flaps 110 of the inverted product package 100 are seated underneath the finger flaps 110', 110" of the two adjacent product packages 100', 100", thereby providing a nesting configuration. This nesting configuration allows the product packages to be readily separated from one another (sequentially removing an outermost product package from the sleeve 190) and concurrently ready for finger gripping the outermost finger flap 110 that remains part of the sleeve 190 (see FIG. 13). In this fashion, when one product package 100' is separated from the other product packages 100, 100" (see FIG. 15) of the sleeve 190, the remaining product packages comprising the sleeve include deployed finger flaps (in this case, 110, 110") ready for finger gripping and successive separation of individual product packages from the remaining sleeve. Post separation of a product package 100' from the remainder of the sleeve 190, the user may follow the foregoing process to grip the pair of opposed finger flaps for each product package to expose and make use of the previously sealed prep pads 108. FIG. 12 depicts a plurality of prep pads 108 being exposed via an exploded longitudinal view to depict the relationship between adjacent product packages and the associate finger flaps 110', 110, 110".

Those skilled in the art will understand that other nesting configurations are within the scope of the disclosure that include, without limitation, using an adhesive to secure adjacent product packages 100 together and/or adjacent finger flaps 110 to one another. By way of example, the adhesive is intended to allow break away of adjacent product packages 100 and/or adjacent finger flaps 110 in order to leave at all times at least one finger flap in a deployed position to allow a user to separate the outermost product package from the remaining sleeve.

Referencing FIGS. 6-9, a second exemplary product package 200 includes complementary sections 202, 204, 206, 208, 210 that are successively sealed together via a series of circumferential seals 212, 214, 216, 218 to define three separate internal cavities. In this exemplary embodiment, the sections 202, 204, 206, 208, 210 may be fabricated from one or more polyesters, a polyethylene (including high, moderate, and low density varieties), aluminum, and a nylons. Moreover, the sections 202, 204, 206, 208, 210 may be fabricated from a single layer of material, multiple layers of same material, or multiple layers of differing materials such as, without limitation, polyethylene layers sandwiching an aluminum layer therebetween. And the circumferential seals 212, 214, 216, 218 may preferably be configured to comprise peelable seals.

Figure 6:
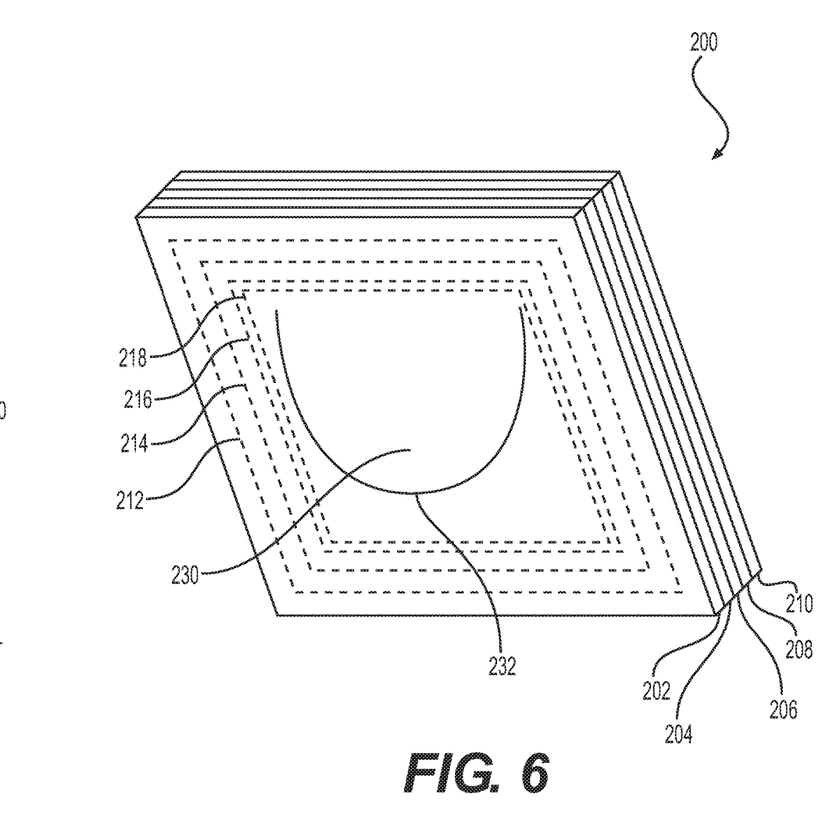
FIG. 6 is an elevated perspective view of a second exemplary product package in accordance with the instant disclosure.
Figure 7:
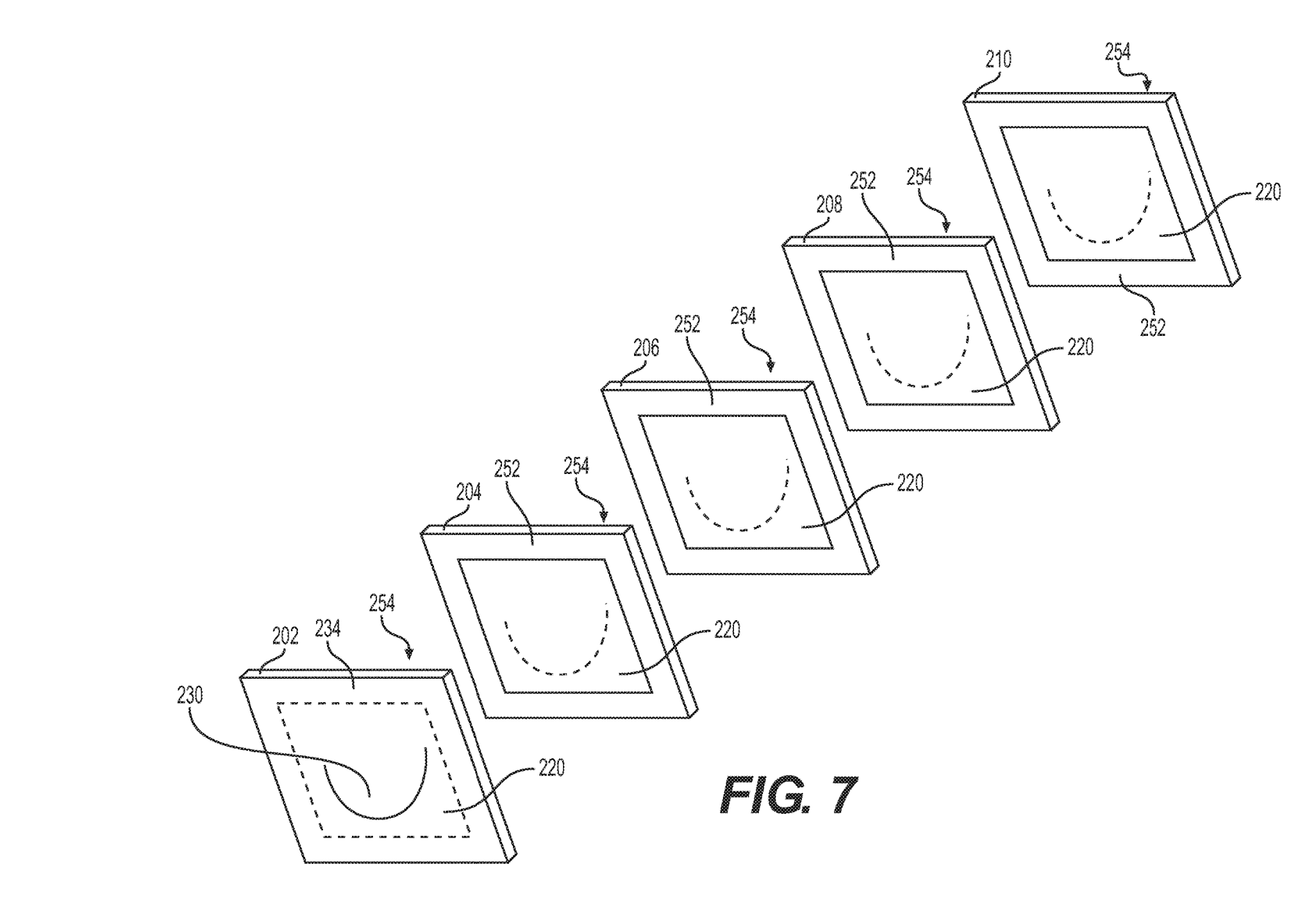
FIG. 7 is an exploded view of the second exemplary product package of FIG. 6.
Figure 8:
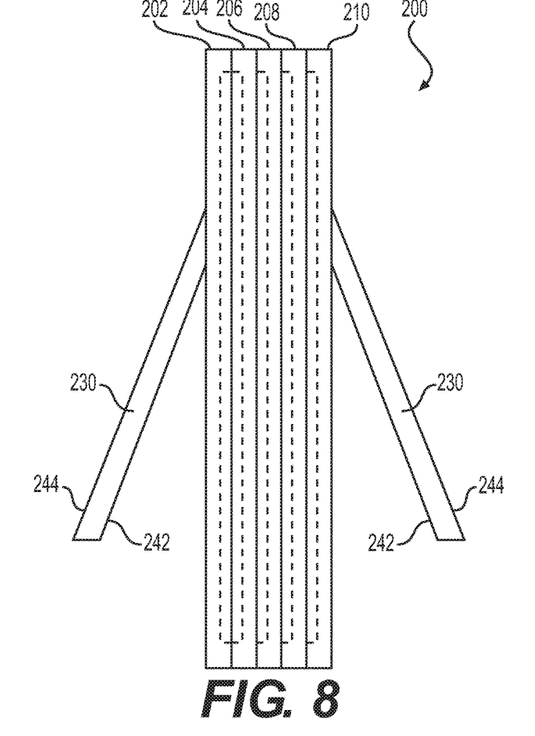
FIG. 8 is a profile view of the second exemplary product package of FIG. 6.

Within each interior cavity may be housed one or more internal contents that include, without limitation, a prep pad 220 fabricated from an absorbent or sponge material. By way of example, the prep pads 220 may entrain any number of fluids or combinations of fluids such as, without limitation, ethanol and/or iodine. Each section 202, 204, 206, 208, 210 includes a finger flap 230 that is repositionable with respect to the remainder of the respective section and is configured to allow finger gripping between a thumb and complementary finger, for example. In exemplary form, the finger flap 230 may be delineated using a cut or slit 232 formed into a respective outer face 234 of that section that allows the finger flap to be integral with the outer face and connected thereto via a living hinge. Alternatively, the finger flap 230 may be a separable component that is mounted to the respective exterior face 234 using any form of attachment such as, without limitation, heat sealing, laser sealing, adhesive bonding, and vibration sealing. In either instance, it is envisioned that the finger flaps 230 are substantially flat or flush with the topography of the exterior faces 234.

In exemplary form, the product packaging 200 may take on a three-dimensional rectangular shape, with each of the sections 202, 204, 206, 208, 210 having a similar shape. In this fashion, the perimeter of the sections 202, 204, 206, 208, 210 are mounted to one another using the series of seals 212, 214, 216, 218 to delineate a series of generally rectangular interior cavities. It should be noted, however, that shapes other than rectangular are within the scope of the disclosure and include, without limitation, circular, triangular, and shapes with more than four perimeter sides. In this fashion, the seals 212, 214, 216, 218 may be rectangular, triangular, circular, or take on any shape desired as long as the shape forms a continuous seal around a perimeter of each of the interior cavities.

The exemplary finger flaps 230 may be grasped and pulled apart as a means to successively break the circumferential seals 212, 214, 216, 218 of the product packaging 200 and expose the internal contents. In exemplary form, a user of the product packaging 200 may reposition a finger underneath an exposed perimeter 232 of each finger flap 230 to reposition the finger flap away from respective sections 202, 204, 206, 208. In so doing, the finger flap 230 protrudes from the sections 202, 204, 206, 208 to expose an underneath face 242 of the finger flap that is generally opposite a top face 244, which top face 244 may have been previously lying on top of or coterminous with an exterior surface 234 of a respective section 202-210. Upon the exposed perimeter 232 of a respective flap 230 achieving a predetermined separation from the exterior face of a respective section 202-210, the user may sandwich the surfaces 242, 244 between opposing digits to grasp the finger flap 230 as a means to reposition one section with respect to another section, thereby breaking a first of the circumferential seals 212, for example. In exemplary form, the user grasps the finger flaps 230 and pulls the flaps away from one another (as denoted by the arrows in FIG. 9) to break the first seal 212 and separate the fourth and fifth sections 208, 210 from one another and expose a prep pad 220. After the first seal 212 is broken, the user may continue to pull the finger flaps 230 to completely separate successive sections 208-204 from one another to expose successive prep pads 220.

Figure 9:
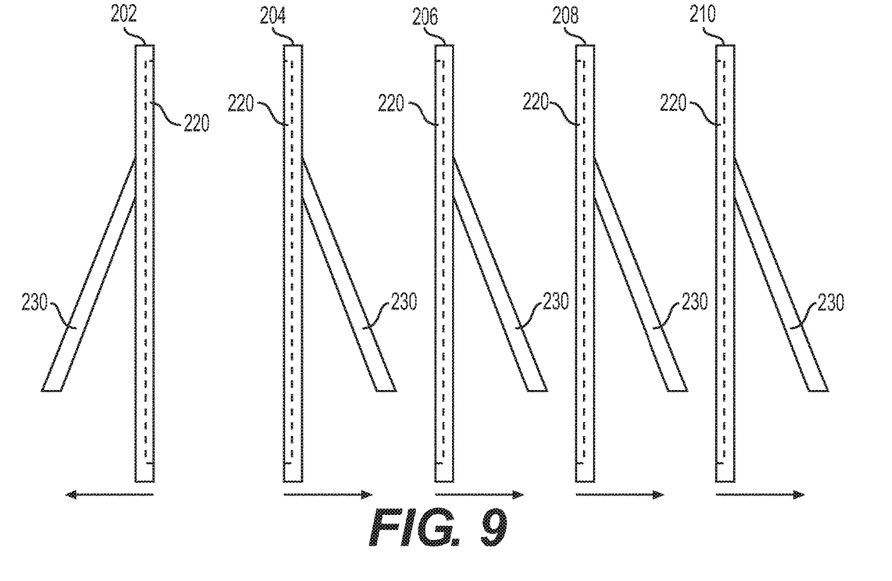
FIG. 9 is a profile view showing intended separation between components of the second exemplary product package of FIG. 6.

In this exemplary embodiment, after the sections 202-210 are completely separated from one another, five prep pads 220 are successively exposed on the interior of the peeled apart sections. By way of example, corresponding prep pads 220 are mounted to corresponding inner faces 252. In this fashion, the inner faces 252 and three of the exterior surfaces 234 cooperate to delineate four interior cavities at least partially occupied by one or two prep pads 220 (the first cavity between the first two sections, 202, 204 includes a pair of prep pads 220). But when a respective seal 212-218 is completely broken, an exposed surface of at least one prep pad 220 becomes available for use (with the final seal 218 exposing two prep pads 220 for use). As a result, the user can maintain grasping of one or both of the finger flaps 230 as a means to reposition the exposed prep pads in contact with the desired tissue or surface without requiring the user's fingers or other body part to contact the prep pad and potentially contaminate the prep pad prior to its intended use. Post repositioning of the prep pads 220, the user may discard each prep pad 220 and corresponding section 210-202 in a trash can or other disposal repository without requiring grasping of the prep pad or regrasping of the finger flap post usage. In other words, the same grasp used to break the circumferential seal 212-218 may be maintained throughout usage of one or all prep pads 220 and throughout discarding the used prep pad(s) 220. This advantageously avoids the user's hands or other unintended body parts from coming into contact with the prep pad 220 prior to, during, and post usage.

Figure 10:
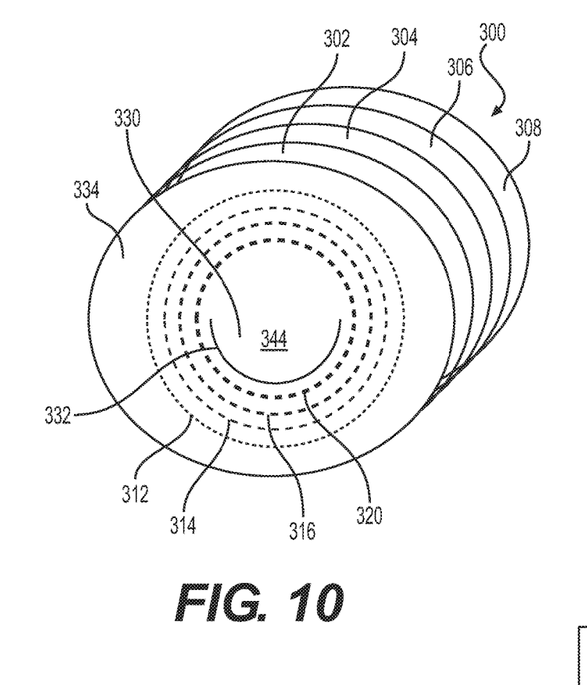
FIG. 10 is an elevated perspective view of a third exemplary product package in accordance with the instant disclosure.

Referencing FIG. 10, a third exemplary product package 300 includes complementary sections 302, 304, 306, 308 that are successively sealed together via a series of concentric circular seals 312, 314, 316 to define three separate internal cavities. In this exemplary embodiment, the sections 302, 304, 306, 308 may be fabricated from one or more polyesters, a polyethylene (including high, moderate, and low density varieties), aluminum, and a nylons. Moreover, the sections 302, 304, 306, 308 may be fabricated from a single layer of material, multiple layers of same material, or multiple layers of differing materials such as, without limitation, polyethylene layers sandwiching an aluminum layer therebetween. And the concentric circular seals 312, 314, 316 may preferably be configured to comprise peelable seals.

Within each interior cavity may be housed one or more internal contents that include, without limitation, a circular prep pad 320 fabricated from an absorbent or sponge material. By way of example, the prep pads 320 may entrain any number of fluids or combinations of fluids such as, without limitation, ethanol and/or iodine. Each section 302-308 includes a finger flap 330 that is repositionable with respect to the remainder of the respective section and is configured to allow finger gripping between a thumb and complementary finger, for example. In exemplary form, the finger flap 330 may be delineated using a cut or slit 332 formed into a respective outer face 334 of that section that allows the finger flap to be integral with the outer wall and connected thereto via a living hinge. Alternatively, the finger flap 330 may be a separable component that is mounted to the respective exterior face 334 using any form of attachment such as, without limitation, heat sealing, laser sealing, adhesive bonding, and vibration sealing. In either instance, it is envisioned that the finger flaps 330 are substantially flat or flush with the topography of the exterior faces 334.

In exemplary form, the product packaging 300 may take on a three-dimensional cylindrical shape, with each of the sections 302-308 having a similar shape. In this fashion, the perimeter of the sections 302-308 are mounted to one another using the series of seals 312-316 to delineate a series of generally circular interior cavities. It should be noted, however, that shapes other than circular are within the scope of the disclosure and include, without limitation, rectangular, triangular, and shapes with more than four perimeter sides. In this fashion, the seals 312-316 may be rectangular, triangular, circular, or take on any shape desired as long as the shape forms a continuous, peelable seal around a perimeter of each of the interior cavities.

The exemplary finger flaps 330 may be grasped and pulled apart as a means to successively break the circumferential seals 312-316 of the product packaging 300 and expose the internal contents. In exemplary form, a user of the product packaging 300 may reposition a finger underneath an exposed perimeter 332 of each finger flap 330 to reposition the finger flap away from respective sections 302-308. In so doing, the finger flap 330 protrudes from the sections 302-308 to expose an underneath face (not shown) of the finger flap that is generally opposite a top face 344, which top face 344 may have been previously lying on top of or coterminous with an exterior face 334 of a respective section 302-308. Upon the exposed perimeter 332 of a respective flap 330 achieving a predetermined separation from the exterior surface of a respective section 302-308, the user may sandwich the surfaces between opposing digits to grasp the finger flap 330 as a means to reposition one section with respect to another section, thereby breaking a first of the circumferential seals 312, for example. In exemplary form, the user grasps the finger flaps 330 and pulls the flaps away from one another to break the first seal 312 and separate the third and fourth sections 308, 306 from one another and expose a prep pad 320. After the first seal 312 is broken, the user may continue to pull the finger flaps 330 to completely separate successive sections 306-302 from one another to expose successive prep pads 320.

In this exemplary embodiment, after the sections 302-308 are completely separated from one another, four prep pads 320 are successively exposed on the interior of the peeled apart sections. By way of example, corresponding prep pads 320 are mounted to corresponding inner faces (not shown). In this fashion, the inner faces and three of the exterior surfaces 234 cooperate to delineate three interior cavities at least partially occupied by one or two prep pads 320 (the first cavity between the first two sections, 302, 304 includes a pair of prep pads 320). But when a respective seal 312-316 is completely broken, an exposed surface of at least one prep pad 320 becomes available for use (with the final seal 316 exposing two prep pads 320 for use). As a result, the user can maintain grasping of one or both of the finger flaps 330 as a means to reposition the exposed prep pads in contact with the desired tissue or surface without requiring the user's fingers or other body part to contact the prep pad and potentially contaminate the prep pad prior to its intended use. Post repositioning of the prep pads 320, the user may discard each prep pad 320 and corresponding section 302-308 in a trash can or other disposal repository without requiring grasping of the prep pad or regrasping of the finger flap post usage. In other words, the same grasp used to break the circumferential seal 312-316 may be maintained throughout usage of one or all prep pads 320 and throughout discarding the used prep pad(s) 320. This advantageously avoids the user's hands or other unintended body parts from coming into contact with the prep pad 320 prior to, during, and post usage.

It should be understood that one or more of the underneath surfaces 120, 242 of a finger flap and the top surfaces 122, 244 of a finger flap may be tacky.

Following from the above description, it should be apparent to those of ordinary skill in the art that, while the methods and apparatuses herein described constitute exemplary embodiments of the present invention, the invention described herein is not limited to any precise embodiment and that changes may be made to such embodiments without departing from the scope of the invention as defined by the claims. Additionally, it is to be understood that the invention is defined by the claims and it is not intended that any limitations or elements describing the exemplary embodiments set forth herein are to be incorporated into the interpretation of any claim element unless such limitation or element is explicitly stated. Likewise, it is to be understood that it is not necessary to meet any or all of the identified advantages or objects of the invention disclosed herein in order to fall within the scope of any claims, since the invention is defined by the claims and since inherent and/or unforeseen advantages of the present invention may exist even though they may not have been explicitly discussed herein.

What is claimed is:

1. A dispensing and applicator system for applying a plurality of applicator pads comprising:
   (a) a first and second moisture impermeable layers removably coupled to one another via a first peelable seal to delineate a first interior cavity;
   (b) a first applicator pad operatively coupled to an interior side of the first moisture impermeable layer and located within the first interior cavity when the first and second moisture impermeable layers are removably coupled to one another;
   (c) a first finger flap operatively coupled to an exterior side of the first moisture impermeable layer and inset within the first peelable seal, where the exterior side of the first moisture impermeable layer is opposite the interior side of the first moisture impermeable layer.

2. The dispensing and applicator system of claim 1, further comprising:
   (d) a third moisture impermeable layer removably coupled to at least one of the first moisture impermeable layer and the second moisture impermeable layer via a second peelable seal to delineate a second interior cavity, wherein the second peelable seal is weaker than the first peelable seal;

(e) a further applicator pad operatively coupled to an interior side of the third moisture impermeable layer and located within the second interior cavity when the third moisture impermeable layer and at least one of the first moisture impermeable layer and the second moisture impermeable layer are removably coupled to one another; and, (f) a further finger flap operatively coupled to an exterior side of the third moisture impermeable layer, where the exterior side of the third moisture impermeable layer is opposite the interior side of the third moisture impermeable layer.

3. The dispensing and applicator system of claim 2, further comprising:

(g) a fourth moisture impermeable layer removably coupled to at least one of the first, second, and third moisture impermeable layers via a third peelable seal to delineate a third interior cavity, wherein the third peelable seal is weaker than the second peelable seal;

(h) a still further applicator pad operatively coupled to an interior side of the fourth moisture impermeable layer and located within the third interior cavity when the fourth moisture impermeable layer is removably coupled to at least one of the first, second, and third moisture impermeable layers; and, (i) a still further finger flap operatively coupled to an exterior side of the fourth moisture impermeable layer, where the exterior side of the fourth moisture impermeable layer is opposite the interior side of the fourth moisture impermeable layer.

4. The dispensing and applicator system of claim 3, further comprising:

(j) a fifth moisture impermeable layer removably coupled to at least one of the first, second, third, and fourth moisture impermeable layers via a fourth peelable seal to delineate a fourth interior cavity, wherein the fourth peelable seal is weaker than the third peelable seal;

(k) an even further applicator pad operatively coupled to an interior side of the fifth moisture impermeable layer and located within the fourth interior cavity when the fifth moisture impermeable layer is removably coupled to at least one of the first, second, third, and fourth moisture impermeable layers; and, (l) an even further finger flap operatively coupled to an exterior side of the fifth moisture impermeable layer, where the exterior side of the fifth moisture impermeable layer is opposite the interior side of the fifth moisture impermeable layer.

5. The dispensing and applicator system of claim 2, wherein at least one of the first peelable seal and the second peelable seal comprises at least one of a laser seal, a sonic induction seal, and a heat seal.

6. The dispensing and applicator system of claim 1, wherein:
the first finger flap is substantially flush with the exterior side of the first moisture impermeable layer.

7. The dispensing and applicator system of claim 1, wherein the first finger flap includes a tacky surface.

8. The dispensing and applicator system of claim 1, wherein at least one of the first and second moisture impermeable layers comprise at least one of a polyester, a polyethylene, aluminum, and a nylon.

9. The dispensing and applicator system of claim 1, wherein at least one of the first and second moisture impermeable layers is adhered to the first applicator pad.

10. The dispensing and applicator system of claim 1, wherein the first applicator pad entrains a fluid.

11. The dispensing and applicator system of claim 1, further comprising:

(i) a third and fourth moisture impermeable layers removably coupled to one another via a second peelable seal to delineate a second interior cavity;

(ii) a second applicator pad operatively coupled to an interior side of the third moisture impermeable layer and located within the second interior cavity when the third and fourth moisture impermeable layers are removably coupled to one another;

(iii) a second finger flap operatively coupled to an exterior side of the third moisture impermeable layer, where the exterior side of the third moisture impermeable layer is opposite the interior side of the third moisture impermeable layer; and, (iv) a third finger flap operatively coupled to an exterior side of the fourth moisture impermeable layer, where the exterior side of the fourth moisture impermeable layer is opposite the interior side of the fourth moisture impermeable layer;

wherein at least one of (a) the first and second finger flaps are operatively coupled to one another, and, (b) the first and third moisture impermeable layers are operatively coupled to one another.

12. The dispensing and applicator system of claim 11, wherein the second finger flap is nested and interposes the first finger flap and the first moisture impermeable layer.

13. The dispensing and applicator system of claim 11, wherein the first finger flap interposes the second finger flap and the third moisture impermeable layer.

14. The dispensing and applicator system of claim 11, further comprising:

(v) a fifth and sixth moisture impermeable layers removably coupled to one another via a third peelable seal to delineate a third interior cavity;

(vi) a further applicator pad operatively coupled to an interior side of the fifth moisture impermeable layer and located within the third interior cavity when the fifth and sixth moisture impermeable layers are removably coupled to one another;

(vii) a fourth finger flap operatively coupled to an exterior side of the fifth moisture impermeable layer, where the exterior side of the fifth moisture impermeable layer is opposite the interior side of the fifth moisture impermeable layer; and, (viii) a fifth finger flap operatively coupled to an exterior side of the sixth moisture impermeable layer, where the exterior side of the sixth moisture impermeable layer is opposite the interior side of the sixth moisture impermeable layer;

wherein at least one of (a) the third and fourth finger flaps are operatively coupled to one another, and, (b) the fourth and fifth moisture impermeable layers are operatively coupled to one another.

15. The dispensing and applicator system of claim 14, wherein the fourth finger flap is nested and interposes the third finger flap and the fourth moisture impermeable layer.

16. The dispensing and applicator system of claim 14, wherein the third finger flap interposes the fourth finger flap and the fifth moisture impermeable layer.

17. The dispensing and applicator system of claim 1, further comprising:

(d) a second applicator pad operatively coupled to an interior side the second moisture impermeable layer and located within the first interior cavity when the first and second moisture impermeable layers are removably coupled to one another;

(e) a second finger flap operatively coupled to an exterior side of the second moisture impermeable layer, where the exterior side of the second moisture impermeable layer is opposite the interior side of the second moisture impermeable layer.

18. The dispensing and applicator system of claim 17, wherein:
the first finger flap is substantially flush with the exterior side of the first moisture impermeable layer; and,
the second finger flap is substantially flush with the exterior side of the second moisture impermeable layer.

19. A method of dispensing one or more applicator pads comprising:
(a) grasping a first finger flap operatively coupled to an exterior side of a first moisture impermeable layer, where the exterior side of the first moisture impermeable layer is opposite an interior side of the first moisture impermeable layer;
(b) grasping a second finger flap operatively coupled to an exterior side of a second moisture impermeable layer, where the exterior side of the second moisture impermeable layer is opposite an interior side of the first moisture impermeable layer;
(c) pulling the first and second finger flaps away from one another to break a first peelable seal between the first moisture impermeable layer and the second moisture impermeable layer to expose a first applicator pad previously sealed between the layers, where at least one of the first and second finger flaps is inset within the first peelable seal.

20. The method of claim 19, wherein pulling the first and second finger flaps away from one another to break the first peelable seal between the first moisture impermeable layer and the second moisture impermeable layer exposes a second applicator pad previously sealed between the layers.

21. The method of claim 20, wherein:
pulling the first and second finger flaps away from one another to break the first peelable seal completely separates the first moisture impermeable layer from the second moisture impermeable layer;
the first applicator pad is operatively coupled to the first moisture impermeable layer post separation of the first and second moisture impermeable layers; and,
the second applicator pad is operatively coupled to the second moisture impermeable layer post separation of the first and second moisture impermeable layers.

22. The method of claim 19, further comprising:
(e) grasping a third finger flap operatively coupled to an exterior side of a third moisture impermeable layer, where the exterior side of the third moisture impermeable layer is opposite an interior side, while grasping the first finger flap;
(f) pulling the first and third finger flaps away from one another to break a second seal between the third moisture impermeable layer and the second moisture impermeable layer to expose a second applicator pad previously sealed between the layers; and,
(g) contacting a second desired surface with the second applicator pad by using the third finger flap, where the third finger flap is fluidically separated from the second applicator pad.

23. The method of claim 22, further comprising:
(h) grasping a fourth finger flap operatively coupled to an exterior side of a fourth moisture impermeable layer, where the exterior side of the fourth moisture impermeable layer is opposite an interior side, while grasping the first finger flap;
(i) pulling the first and fourth finger flaps away from one another to break a third seal between the third moisture impermeable layer and the fourth moisture impermeable layer to expose a third applicator pad previously sealed between the layers; and,
(j) contacting a third desired surface with the third applicator pad by using the fourth finger flap, where the fourth finger flap is fluidically separated from the third applicator pad.

24. A method of fabricating a dispensing system for one or more applicator pads, the method comprising:
(a) providing a first moisture impermeable layer that includes an interior face and an opposite exterior face, wherein the exterior face is operatively coupled to a first finger flap;
(b) providing a second moisture impermeable layer that includes an interior face and an opposite exterior face, wherein the exterior face is operatively coupled to a second finger flap; and,
(c) sealing a first applicator pad between interior faces of the first and second moisture impermeable layers using a first peelable seal that surrounds at least one of the first and second finger flaps.

25. The method of claim 24, further comprising:
(d) providing a third moisture impermeable layer that include an interior face and an opposite exterior face, wherein the exterior face is operatively coupled to a third finger flap; and,
(e) sealing a second applicator pad between the interior face of the third moisture impermeable layer and the exterior face of the second moisture impermeable layer using a second peelable seal, where second peelable seal between the second and third moisture impermeable layers is weaker than the first peelable seal between the first and second moisture impermeable layers.

26. The method of claim 25 further comprising:
(f) providing a fourth moisture impermeable layer that include an interior face and an opposite exterior face, wherein the exterior face is operatively coupled to a fourth finger flap; and,
(g) sealing a third applicator pad between the interior face of the fourth moisture impermeable layer and the exterior face of the third moisture impermeable layer using a third peelable seal, where the third peelable seal between the fourth and third moisture impermeable layers is weaker than the second peelable seal between the third and second moisture impermeable layers.

27. The method of claim 24, wherein:
the first applicator pad includes a pair of applicator pads;
one of the pair of applicator pads is mounted to the interior face of the first moisture impermeable layer; and,
another of the pair of applicator pads is mounted to the interior face of the second moisture impermeable layer.

28. The method of claim 24, wherein at least one of the first finger flap and the second finger flap includes a living hinge.

29. The method of claim 24, wherein:
consecutively repeating steps (a) through (c) to generate a plurality of prep pad packages, where each set of steps (a) through (c) generates one of the plurality of prep pad packages; and,
orienting the plurality of prep pad packages so that every other one is inverted and the first finger flap of one of the plurality of prep pad packages interposes the second finger flap and the second moisture impermeable layer of another of the plurality of prep pad packages.

\* \* \* \* \*